United States Patent
Anderson et al.

(10) Patent No.: US 10,288,595 B2
(45) Date of Patent: May 14, 2019

(54) WATER QUALITY ANALYSIS SYSTEM AND METHOD

(71) Applicants: Michael J. Anderson, Dumfries, VA (US); Clint B. Smith, Chantilly, VA (US); Andmorgan R. Fisher, Haymarket, VA (US); Tung Ly, Lorton, VA (US)

(72) Inventors: Michael J. Anderson, Dumfries, VA (US); Clint B. Smith, Chantilly, VA (US); Andmorgan R. Fisher, Haymarket, VA (US); Tung Ly, Lorton, VA (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 253 days.

(21) Appl. No.: 14/717,314

(22) Filed: May 20, 2015

(65) Prior Publication Data

US 2018/0059085 A1  Mar. 1, 2018

(51) Int. Cl.
*G01N 33/18* (2006.01)
*G01N 33/24* (2006.01)

(52) U.S. Cl.
CPC ..... *G01N 33/1886* (2013.01); *G01N 33/1893* (2013.01); *G01N 2033/243* (2013.01)

(58) Field of Classification Search
CPC . G01N 33/18; G01N 33/1886; G01N 33/1893
USPC ............ 73/61.41, 61.56, 61.57, 61.58, 61.61
See application file for complete search history.

(56) References Cited

U.S. PATENT DOCUMENTS

| | | | | |
|---|---|---|---|---|
| 5,979,219 | A * | 11/1999 | Sellmer-Wilsberg | B01D 61/362 73/19.12 |
| 6,536,272 | B1 * | 3/2003 | Houston | G01N 1/12 702/2 |
| 2003/0042149 | A1 * | 3/2003 | Smith | G01N 27/4163 205/775 |
| 2005/0247114 | A1 * | 11/2005 | Kahn | G01N 33/18 73/53.01 |

\* cited by examiner

*Primary Examiner* — Benjamin R Schmitt
(74) *Attorney, Agent, or Firm* — Brian C. Jones

(57) ABSTRACT

The present invention provides a water quality analysis system capable of making multiple simultaneous measurements of different water quality parameters and saving or transmitting this data for analysis. A housing surrounds a data processor and a water sensor flow cell. The flow cell incorporates a channel through which a stream of water flows. Multiple probe bores within the flow cell house different sensor probes used to measure different water quality parameters of the stream. The data processor receives and digitizes data for the different water quality parameters.

15 Claims, 3 Drawing Sheets

WATER QUALITY ANALYSIS SYSTEM AND METHOD

The invention described herein was made by employees of the United States Government and may be manufactured and used by the Government of the United States of America for governmental purposes without the payment of any royalties thereon or therefore.

BACKGROUND OF THE INVENTION

1. Field of Invention

This invention relates to the field of measuring and testing and more specifically to liquid analysis.

2. Description of Related Art

Water purification processes require validation by testing samples both before and after the purification process to ensure that the water meets specific standards for quality. Typical parameters relied upon for testing water quality after purification to determine if the process was successful include water temperature, pH, conductivity and turbidity. Testing of all of these measured parameters is accomplished by the use of sensors.

Water testing sensors known in the art are difficult to use for taking continuous measurements. Most sensors must be set up individually, and measure only a single parameter at a time. Manifolds that allow deployment of multiple sensors simultaneously require advance set-up and deployment and have limited applicability with respect to fieldwork because they are not designed for all-inclusive flow characteristics. Furthermore, existing systems are not designed to integrate multiple types of data, nor are they designed for general-purpose use.

There is an unmet need in the art for a compact water quality analysis system capable of measuring and transmitting multiple water quality parameters simultaneously over a continuous period.

BRIEF SUMMARY OF THE INVENTION

In one embodiment of the invention, a water sensor flow cell apparatus includes a manifold body, a water channel within the manifold body and a plurality of probe bores within the manifold body that are operably connected to the water channel. The water channel extends between a cell inlet and a cell outlet. At least one of the plurality of probe bores within the manifold body operably connects to the water channel at a non-zero angle. Each of the plurality of probe bores contains at least one sensor probe in communication with the water channel.

In another embodiment of the invention, a water quality analysis system includes a water sensor flow cell apparatus as above, a data processor and a housing. The data processor operatively connects to at least one sensor probe and has a receiver configured to receive data from at least one sensor probe. The housing surrounds the water sensor flow cell apparatus and the data processor, and includes a housing inlet and a housing outlet.

In another embodiment of the invention, a method of using a water quality analysis system includes the following steps. The method receives a volume of water flowing as a water stream through a water channel within a manifold body. The water channel extends between a cell inlet and a cell outlet. Next, the method continuously measures at least one parameter of the water stream using at least one sensor probe in contact with the water stream. At least one sensor probe is contained by one of a plurality of probe bores within the manifold body. At least one of the plurality of probe bores operably connects to the water channel at a non-zero angle. The method then continuously transmits data values of at least one parameter from at least one sensor probe to a data processor. Next, the method digitizes the data values.

BRIEF DESCRIPTION OF SEVERAL VIEWS OF THE DRAWING(S)

TERMS OF ART

As used herein, the term "multi-path channel" means a channel wherein a water stream moves along a curved, split or serpentine path, along multiple paths or any combination of the foregoing.

As used herein, the term "sensor probe" means a sensor capable of sensing at least one parameter of a volume of water.

As used herein, the term "single-path channel" means a channel wherein a water stream moves along a straight or angled path.

DETAILED DESCRIPTION OF THE INVENTION

Figure 1:
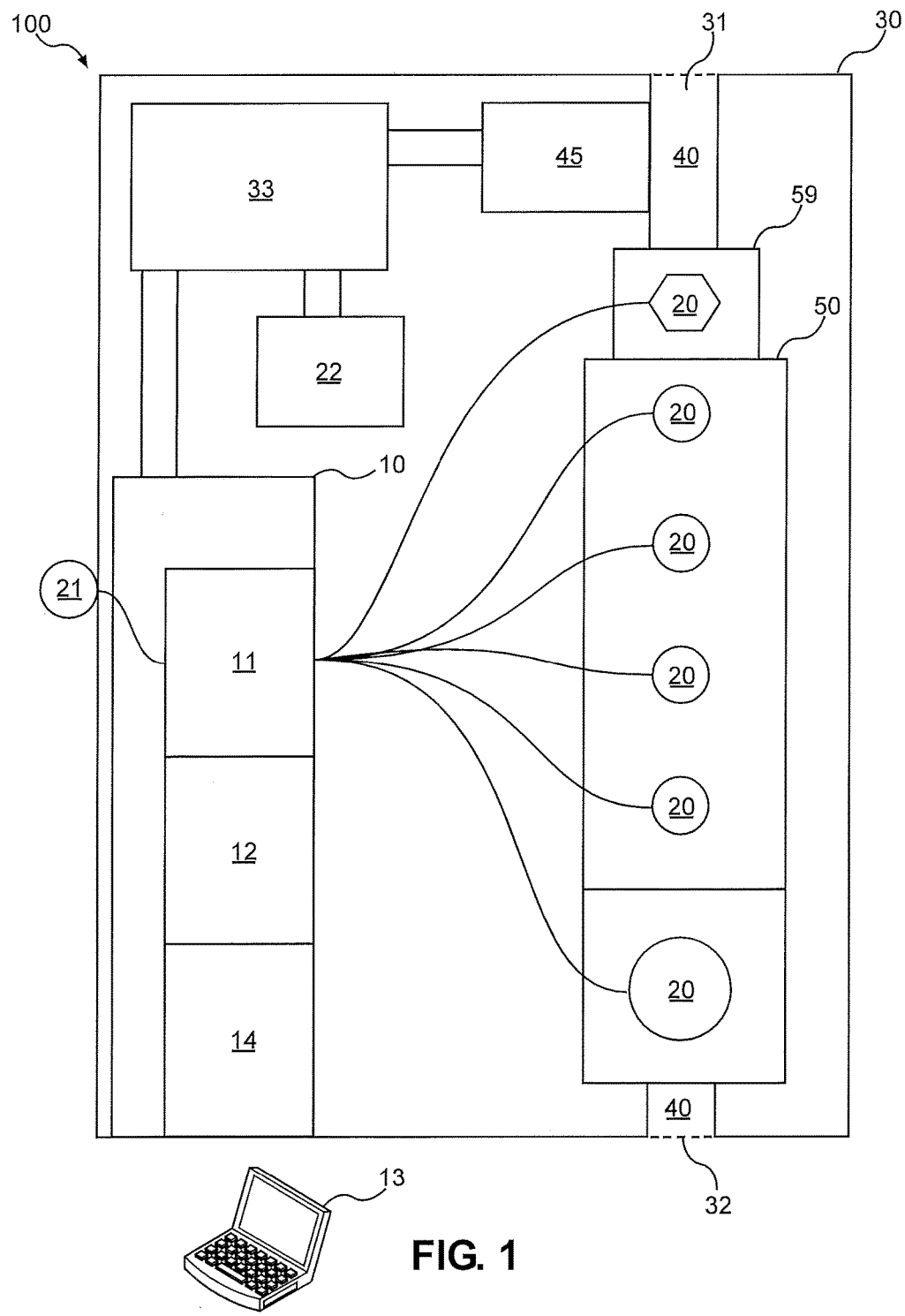
FIG. 1 illustrates an exemplary embodiment of a water quality analysis system.

FIG. 1 illustrates an exemplary embodiment of a water quality analysis system 100. System 100 includes a data processor 10, at least one sensor probe 20, a housing 30, connective tubing 40 and a water sensor flow cell 50.

In the exemplary embodiment, data processor 10 includes a receiver 11 coupled to at least one sensor probe 20 by a wired or wireless connection. Receiver 11 receives data values from at least one sensor probe 20 for processing, including digitizing. In one embodiment, processed data may be stored in memory 12 of data processor 10. In another embodiment, transmitter 14 transmits data to an external device 13. In the exemplary embodiment, external device 13 is a computer, such as, but not limited to, a laptop computer. In other embodiments, external device 13 is a smart device, such as, but not limited to, a smart phone.

In the exemplary embodiment, sensor probe 20 includes five sensor probes. Other embodiments may include between approximately 1 and approximately 30 sensor probes 20. In the exemplary embodiment, sensor probes 20 measure water temperature, pH, conductivity and turbidity. Other embodiments may include additional or different sensor probes 20 configured to measure other water qualities such as, but not limited to oxidation-reduction potential, total dissolved solids, dissolved oxygen, free chlorine, free arsenic, free cyanide, water flow, blue-green algae concentration, Chlorophyll a concentration, total dissolved gas and specific ion concentrations such as, but not limited to heavy metals, ammonia, ammonium, nitrate, nitrite, chloride and phosphate. Certain embodiments also include at least one external sensor 21 such as, but not limited to a positional accelerometer or a sensor measuring photosynthetic active radiation, air temperature, humidity, precipitation and wind speed. Certain embodiments also include a global positioning unit 22.

In the exemplary embodiment, housing 30 includes housing inlet 31, housing outlet 32 and power source 33. Housing 30 may be a polymer, composite or metal casing surrounding the remainder of system 100. In the exemplary embodiment, housing inlet 31 connects to a source of water for testing, conveying the water to water sensor flow cell 50 through tubing 40. In the exemplary embodiment, water pump 45 forces water through tubing 40.

Water exiting water sensor flow cell 50 travels through additional tubing 40 to housing outlet 32 for disposal, use or treatment. In other embodiments, housing inlet 31 and housing outlet 32 connect directly to water sensor flow cell 50. Power source 33 provides power to data processor 10 and sensor probes 20 as needed. In the exemplary embodiment, power source 33 is a battery. In other embodiments, power source 33 may be, but is not limited to, a connection to a power line, external battery or generator.

Figure 2:
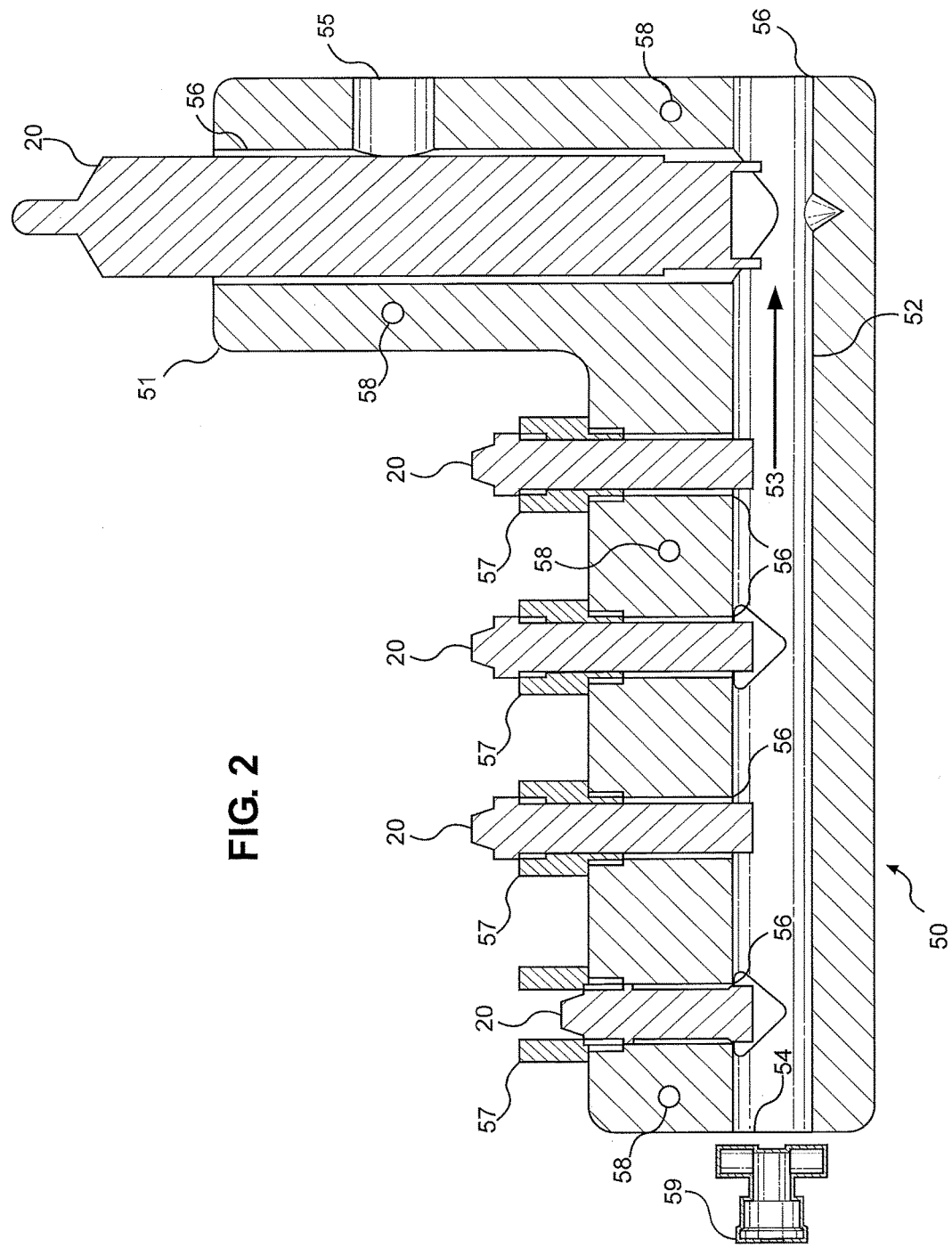
FIG. 2 illustrates an exemplary embodiment of a water sensor flow cell for a water quality analysis system.

FIG. 2 illustrates an exemplary embodiment of water sensor flow cell 50 for water quality analysis system 100. In the exemplary embodiment, water sensor flow cell 50 includes manifold body 51, water channel 52, cell inlet 54, cell outlet 55, a plurality of probe bores 56 with corresponding probe caps 57, and a plurality of fastening bores 58.

Water channel 52 extends through manifold body 51 between cell inlet 54 and cell outlet 55. In the exemplary embodiment, water channel 52 is a single-path channel. In other embodiments, water channel 52 is a multi-path channel. Water stream 53 flows through water channel 52.

In the exemplary embodiment, manifold body 51 is manufactured from a non-oxidizing metal. Because these metals do not dissolve, they do not alter the content of water stream 53. These metals include, but are not limited to titanium, aluminum, stainless steel, platinum, iridium, palladium and any combination thereof. In other embodiments, manifold body 51 is manufactured from a non-oxidizing polymer such as, but not limited to polyacetal and polyvinyl chloride. Other embodiments incorporate non-oxidizing, non-water soluble polymers into manifold body 51 as a coating on inner surfaces of manifold body 51. These polymers include, but are not limited to silicone, polyethylene, polytetrafluoroethylene and polypropylene.

In the exemplary embodiment, cell inlet 54 and cell outlet 55 connect to housing inlet 31 and housing outlet 32, respectively, via tubing 40. In other embodiments, cell inlet 54 and cell outlet 55 connect directly to housing inlet 31 and housing outlet 32, respectively. Cell outlet 55 is located above cell inlet 54 to reduce air bubbles and head space in water channel 52.

At least one of probe bores 56 forms a non-zero angle with a segment of water channel 52 within manifold body 51. In the exemplary embodiment, this angle is approximately 90 degrees. Probe bores 56 allow insertion of at least one sensor probe 20 so that at least one sensor probe 20 is in communication with water channel 52 and contacts water stream 53 as it flows through water channel 52. Probe bores 56 do not necessarily have a uniform shape, cross-sectional size or length between probe bores 56, allowing them to accommodate sensor probes 20 of varying shape and size. Probe bores 56 may have a diameter of approximately 0.2 inches to approximately 1.5 inches. Probe bores 56 may have a length of approximately 0.5 inches to approximately 4.0 inches. In the exemplary embodiment, probe bores 56 number 4. In other embodiments, probe bores 56 may number between 2 and 30.

Probe caps 57 sealably and removably hold sensor probes 20 in place to ensure adequate contact with water flow without water loss from probe bores 56. Probe caps 57 also allow removal and replacement of sensor probes 20 to permit calibration of sensor probes 20, replacement of malfunctioning sensor probes 20 or to change the overall sensing capabilities of system 100. Fastening bores 58 accommodate fasteners to hold water sensor flow cell 50 in place within housing 30.

The exemplary embodiment includes at least one detachable bore 59, which can add a new probe bore 56 to water sensor flow cell 50. In the exemplary embodiment, detachable bore 59 removably attaches to cell inlet 54. Probe bore 56 of detachable bore 59 has a different configuration than probe bores 56 found in manifold body 51, thereby allowing use of a differently configured sensor probe 20.

Figure 3:
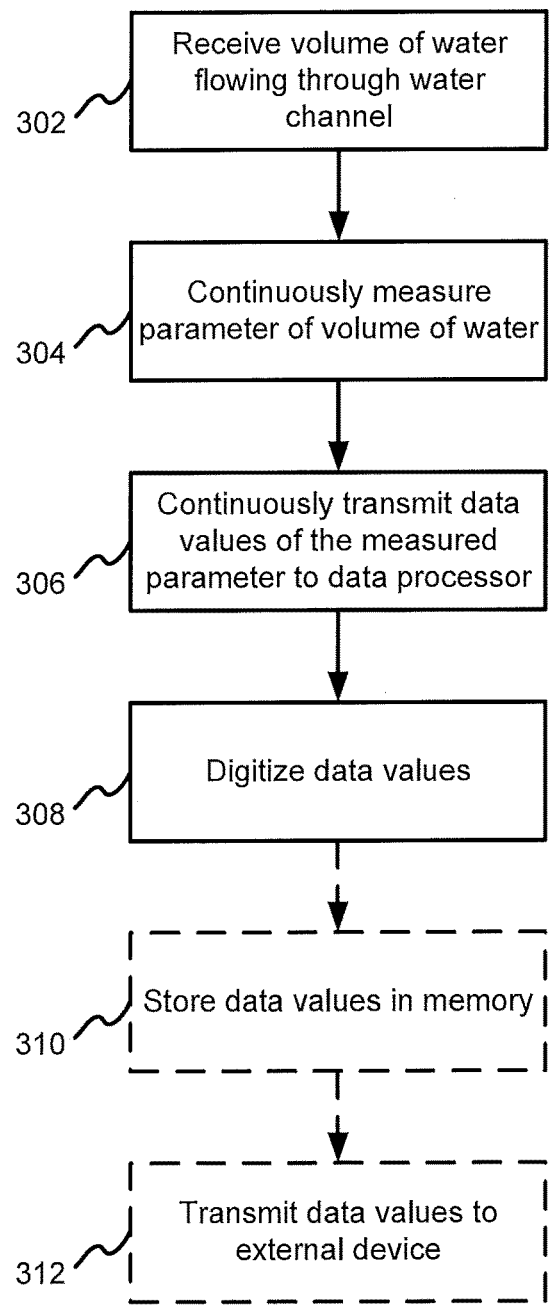
FIG. 3 illustrates flowchart of an exemplary embodiment of a method of using a water quality analysis system.

FIG. 3 illustrates flowchart of an exemplary embodiment of a method 300 of using water quality analysis system 100.

In step 302, method 300 receives a volume of water flowing through water channel 52.

In step 304, at least one sensor probe 20 continuously measures a parameter of the volume of water.

In step 306, at least one sensor probe 20 continuously transmits data values of the measured parameter to data processor 10.

In step 308, data processor 10 digitizes the data values.

In optional step 310, data processor 10 stores the data values in memory 12.

In optional step 312, data processor 10 transmits the data values to external device 13.

It will be understood that many additional changes in the details, materials, procedures and arrangement of parts, which have been herein described and illustrated to explain the nature of the invention, may be made by those skilled in the art within the principle and scope of the invention as expressed in the appended claims.

It should be further understood that the drawings are not necessarily to scale; instead, emphasis has been placed upon illustrating the principles of the invention. Moreover, the terms "about," "substantially" or "approximately" as used herein may be applied to modify any quantitative representation that could permissibly vary without resulting in a change in the basic function to which it is related.

What is claimed is:

1. A water sensor flow cell apparatus, comprising:
   a manifold body;
   a water channel within said manifold body, wherein said water channel extends between a cell inlet and a cell outlet wherein said cell outlet is located above said cell inlet; and
   a plurality of probe bores within said manifold body operably connected to said water to channel, wherein at least one of said plurality of probe bores operably connects to said water channel at a non-zero angle, wherein at least one of said plurality of probe bores contains at least one sensor probe in communication with said water channel, wherein at least one of said plurality of probe bores has a shape, cross-sectional size or length different from a shape, cross-sectional size or length of another of said plurality of probe bores; and wherein said at least one sensor probe is operatively connected to one of a plurality of probe caps, each of said plurality of probe caps is sealably and removably connected to one of said plurality of probe bores, and said plurality of probe caps sealably and removably hold said at least one sensor probe, extending through said probe cap, in place.

2. The water sensor flow cell apparatus of claim 1, wherein said manifold body comprises a non-oxidizing metal selected from the group consisting of: titanium, aluminum, stainless steel, platinum, iridium, palladium and combination thereof.

3. The water sensor flow cell apparatus of claim 1, wherein said manifold body comprises a non-oxidizing polymer selected from the group consisting of: polyacetal, polyvinyl chloride, polytetrafluoroethylene, silicone, polyethylene and polypropylene.

4. The water sensor flow cell apparatus of claim 1, wherein said plurality of probe bores number between 2 and 30.

5. The water sensor flow cell apparatus of claim 1, wherein said at least one sensor probe is configured to measure at least one parameter selected from the group consisting of: water temperature, pH, conductivity and turbidity, oxidation-reduction potential, total dissolved solids, dissolved oxygen, free chlorine, free arsenic, free cyanide, water flow, blue-green algae concentration, Chlorophyll a concentration, total dissolved gas and specific ion concentration.

6. The water sensor flow cell apparatus of claim 1, wherein said water channel is a single-path channel.

7. The water sensor flow cell apparatus of claim 1, wherein said water channel is a multi-path channel.

8. A water quality analysis system, comprising:
a water sensor flow cell apparatus according to claim 1, and further comprising:
a data processor operatively connected to said at least one sensor probe and having a receiver configured to receive data from said at least one sensor probe;
a housing surrounding said water sensor flow cell apparatus and said data processor, wherein said housing comprises a housing inlet and a housing outlet.

9. The water quality analysis system of claim 8, wherein said data processor further comprises a memory configured to store said data.

10. The water quality analysis system of claim 8, wherein said data processor further comprises a transmitter configured to transmit said data to an external device.

11. The water quality analysis system of claim 10, wherein said external device is selected from the group consisting of a smart device and a computer.

12. The water quality analysis system of claim 8, further comprising tubing connecting said housing inlet to said cell inlet and connecting said housing outlet to said cell outlet.

13. The water quality analysis system of claim 8, further comprising a power source operatively connected to said plurality of sensor probes and to said data processor.

14. The water quality analysis system of claim 8, further comprising a detachable probe bore.

15. The water sensor flow cell apparatus of claim 1, further comprising a detachable probe bore.

* * * * *